US006967025B2

(12) United States Patent
Di Cintio et al.

(10) Patent No.: US 6,967,025 B2
(45) Date of Patent: Nov. 22, 2005

(54) ARTICLES WITH SPORES EXHIBITING ANTAGONISTIC PROPERTIES AGAINST PATHOGENS AND/OR SPORES FORMING MICRO-ORGANISMS

(75) Inventors: Achille Di Cintio, Pescara (IT); Antonella Pesce, Pescara (IT); Giovanni Carlucci, Chieti (IT); Donatella Talone, Chieti (IT)

(73) Assignee: The Procter & Gamble Company, Cincinnati, OH (US)

( * ) Notice: Subject to any disclaimer, the term of this patent is extended or adjusted under 35 U.S.C. 154(b) by 239 days.

(21) Appl. No.: 10/181,396

(22) PCT Filed: Jan. 17, 2001

(86) PCT No.: PCT/US01/01465

§ 371 (c)(1),
(2), (4) Date: Jul. 17, 2002

(87) PCT Pub. No.: WO01/52913

PCT Pub. Date: Jul. 26, 2001

(65) Prior Publication Data

US 2003/0003138 A1    Jan. 2, 2003

(30) Foreign Application Priority Data

Jan. 18, 2000  (EP) .................................. 00100258
Jan. 18, 2000  (EP) .................................. 00100260
Jan. 18, 2000  (EP) .................................. 00100261

(51) Int. Cl.$^7$ ........................................... A01N 25/34
(52) U.S. Cl. ..................................................... 424/402
(58) Field of Search ........................................ 424/402

(56) References Cited

U.S. PATENT DOCUMENTS

| 5,275,943 A | 1/1994 | DiTuro |
| 5,429,628 A * | 7/1995 | Trinh et al. ................. 604/359 |
| 6,710,219 B2 | 3/2004 | Persson |

FOREIGN PATENT DOCUMENTS

| EP | 0 811 392 A1 | 12/1997 |
| JP | 61275401 | 12/1986 |
| SE | 8505491 | 5/1987 |
| WO | WO 92/13577 A1 | 8/1992 |
| WO | WO 98/47374 A1 * | 10/1998 |
| WO | WO 99/17813 A1 * | 4/1999 |
| WO | WO 99/45099 A1 | 9/1999 |

* cited by examiner

*Primary Examiner*—Thurman K. Page
*Assistant Examiner*—Sharon Howard
(74) *Attorney, Agent, or Firm*—Bridget D. Murray; Kevin C. Johnson (57) ABSTRACT

The present invention relates to disposable absorbent articles like sanitary napkins and pantiliners, which comprise spore-forming micro-organisms and/or spores which have the ability to germinate into microorganisms which exhibit antagonistic properties against undesirable strains of micro-organisms when the articles are in use. The invention provides storage-stable disposable absorbent articles which can be worn for long periods of time with reduced generation of undesirable odors and enhanced fluid (e.g., bodily fluid) control within the articles.

7 Claims, 1 Drawing Sheet

Fig. 1

ARTICLES WITH SPORES EXHIBITING ANTAGONISTIC PROPERTIES AGAINST PATHOGENS AND/OR SPORES FORMING MICRO-ORGANISMS

FIELD OF THE INVENTION

This invention relates to an article, such as a disposable absorbent article, intended to be brought into contact with a user's skin, for example the skin in the perineum, this article comprising spores which in their living form exhibit antagonistic properties against undesirable strains of micro-organisms and/or spore-forming micro-organisms exhibiting antagonistic properties against undesirable strains of microorganisms.

BACKGROUND OF THE INVENTION

Hygiene articles like pantiliners, sanitary napkins, tampons, diapers and so on are used to absorb/retain bodily discharge. A problem associated with bodily discharge (vaginal discharge including vaginal fluids, and/or menstruation, urinal discharge, faeces or perspiration) is the generation of undesirable odors within such hygiene articles that have the tendency to escape out of the articles.

Many products and articles are available which aim to prevent the occurrence of malodours and/or to avoid and minimise the detection of malodours typically associated with bodily discharge.

Various odour control materials have been disclosed in the art to combat some of the unpleasant odours associated with body fluid discharges. Indeed solutions have been provided that use different technical approaches like masking, i.e., covering the odour with a perfume, or absorbing the odour already present in the bodily fluids and those generated after degradation, or preventing the formation of the odour.

Most of the focus in the prior art is found on the odour absorption technology. Examples of these types of compounds include activated carbons, clays, zeolites, silicates, absorbing gelling materials, starches, cyclodextrine, ion exchange resins and various mixture thereof as for example described in EP-A-348 978, EP-A-510 619, WO 91/12029, WO 91/11977, WO 89/02698, and/or WO 91/12030. All of these types of odour control agents are believed to control odour by mechanisms whereby the malodorous compounds and their precursors are physically absorbed by the agents and thereby hinder the exit of the odour from articles like absorbent articles. However, such mechanisms are not completely effective as the formation of the odour itself is not prevented and thus odour detection is not completely avoided. Also the drawback with these odour-absorbing agents is that, the bacteria are still able to grow, and the use of bacteria inhibiting agents, which are often selective, can create risks, for instance, in the form of allergenic properties or negative ecological consequences when handling waste. Furthermore, the use of bacteria inhibiting agents involves the risk that resistant strains will occur.

It is known within the medicine and foodstuff technologies to use bioconservation with the aid of bacterial antagonism as a conserving method, and to inoculate special bacteria strains to favourize bacteria populations that are beneficial to the stomach and intestines, for health-promoting purposes. Examples in this respect are conventional yogurt and soured milk, and also novel bioactive foodstuffs. This methodology also includes the use of bacteria such as so-called probiotic bacteria as a substitute for antibiotic bacteria.

International Patent Application WO 92/13577 describes a tampon or sanitary napkin that has been impregnated with a culture of lactic-acid producing bacteria, preferably of the genus Pediococcus, isolated from healthy individuals. The tampon or sanitary napkin is intended for the prophylactic treatment of urogenital infections. WO 97/02846 discloses an absorbent article with antagonistic microorganisms selected from the family Lactobacillaceae, preferably from the genera *Lactobacillus* or *Lactococcus*.

However, the problem encountered with such articles of the prior art is the stability of the articles both during storage and use. None of these prior art documents discloses anything about providing articles, especially disposable absorbent articles, which exhibit antagonistic properties against undesirable pathogens, which articles can be stored for a long time and still contain a sufficient amount of active and transferable bacteria. It is absolutely necessary that consumer products such as disposable absorbent articles can be stored for a long time and under non-ideal conditions without risking that the quality of the articles is impaired. Consequently, there is a need for articles delivering antagonistic properties against pathogens, which articles are specially adopted for long-time storage under unfavorable conditions and for maintaining their antagonistic properties against pathogens in use.

An attempt has been made in this direction in WO 99/17813 which discloses absorbent articles with a suspension of lactic acid bacteria from the genera *Lactobacillus*, *Lactococcus* or *Pediococcus*, the article being dried after application of the suspension, to a moisture content of less than 10% calculated as percentage of weight of the absorbent core in the article. However such articles do not fully meet the problems mentioned herein before. Also the production of such articles requires an extra drying step which impairs on the manufacturing requirements of speed and cost.

The object of the present invention is to provide an article for external application to a human or animal, without permitting pathogenic microorganisms to grow or to become active to an extent such as to promote undesirable odours.

More particularly, it is an object of the present invention to provide disposable absorbent articles which deliver a broader spectrum of odour control mainly by preventing the formation of malodours while not compromising on the overall protection delivered by such articles or even improving protection (e.g., reducing wet through and/or reducing re-wetting).

It is a further object of the present invention to provide such articles which are stable over prolonged time of storage without risking that the quality of the articles is impaired.

Yet, it is a further object of the present invention to provide articles which deliver a sustained antagonistic effect against undesirable strains of microorganisms. More particularly it is an object of the present invention to provide articles, especially disposable absorbent articles, which deliver a sustained odour control over prolonged use time of the articles, i.e., a long lasting odour control by preventing the formation of odour over prolonged wearing time of the articles.

Finally, it is an object of the present invention to provide articles, especially disposable absorbent articles, having the benefits mentioned herein before while meeting the requirements of ease of manufacturing, time effectiveness and cost effectiveness.

These objects have been achieved in accordance with the present invention by providing a disposable article comprising an absorbent core containing spores which are able to germinate under favorable conditions (typically in use conditions, e.g., when the article is applied to the external surface of a human or animal) in microorganisms (i.e., the corresponding living form of the spores) which exhibit antagonistic properties against undesirable strains of micro-organisms, typically present or arisen in the article upon contact with bodily fluids.

The living form of the spores have an activity such as to restrain the growth of undesirable strains of microorganisms or establishing of new undesirable species of microorganisms. Even some killing of microorganisms of undesirable species may occur. Indeed, the living form of the spores used in the present invention have the ability to inhibit undesirable strains of micro-organisms by competing for substrate. The antagonistic properties of the living form of the spores used herein is further partly denoted their ability of producing different so called antimetabolites, such as lactic acid, lactoperoxidases, bacteriocins and carbon dioxides.

More particularly, it has been surprisingly discovered that the use, in the absorbent core of an disposable absorbent article, of spores of micro-organisms which exhibit antagonistic properties against undesirable pathogens (preferably *B coagulans* spores also called herein after *L. sporogenes*), provides an effective odour controlling article which can be stored for long time periods before its actual use, without risking that the odour control ability of the article in use is impaired. The use of these spores able storage stability upon prolonged periods of time up to the time the article is used, i.e., is applied on the external surface of a human or animal body where it typically comes into contact with bodily fluids, and undergoes environmental changes that will create favourable environmental condition for the germination of the spores. In use conditions, for example when a disposable article is applied onto the skin or in the urogenital zone, the body temperature, the micro-environmental humidity and the availability of nutriments like menses, vaginal discharge, urine, perspiration and the like, will allow transformation/germination of the spores (dormant form) in the microorganisms (living form).

Advantageously, the spore-containing articles according to the present invention retain their whole antagonistic properties against pathogens like the odour control capacity up to the time their are used. Thus the present invention also allows to provide articles with effective antagonistic properties, e.g., odour controlling ability, while using reduced total amount of active material (typically odour control material). Indeed a reduced total amount of spores according to the present invention is needed to obtain a given odour control activity for a given disposable article as compared to the total amount of non-spore forming antagonistic micro-organisms like *Lactobacillus, Pediococcus,* or *Lactococcus* that would be needed to get the same activity.

In one aspect of the present invention the disposable absorbent article will comprise within its absorbent core spore-forming microorganisms (living form of the microorganisms) exhibiting antagonistic properties against undesirable strains of microorganisms as an alternative or in mixture with the spores described herein.

Advantageously the spore-forming micro-organisms able to exhibit antagonistic properties against pathogens used herein, preferably the species *B. coagulans,* have the ability to create very quickly an environment that is not suitable for the growth of pathogens. This is due to the rapid growth, high yield and reproducibility of such micro-organisms in comparison to non-spore forming bacteria like *Lactobacillus acidophilus.* The spore forming micro-organisms used herein are able to survive longer and reproduce themselves in comparison to non spore-forming micro-organisms. In other words, by the formation of spores these micro-organisms can germinate and re-germinate in time sequence in line with the bodily fluid discharge (growth media) into an absorbent article, thereby ensuring long-lasting antagonistic properties against pathogens.

Without to be bound by theory, it is speculated herein that in the event where the bodily fluid discharge is reduced and hence less substrate is available for the micro-organisms, the micro-organisms used herein have the ability to be transformed in a dormant form, i.e., spore form, which will be activated again upon availability of further substrate, typically upon further bodily fluid discharge. Thus also when providing the disposable absorbent articles with the living form, i.e. the spore forming micro-organisms, effective antagonistic properties, e.g., odour controlling ability, while using reduced total amount of active material (typically odour control material).

It is an advantage of the present invention to provide a disposable absorbent article which can be worn for a relatively long period of time without microorganisms being allowed to grow to an extent in which undesirable odours are generated. Advantageously the genetic identity, the lactic acid producing ability, the viability as well as the valuable antagonistic properties against pathogens are maintained even upon prolonged periods of use, typically during the whole wearing time of the article, e.g., up to 1 hour to 10 hours as need arises.

A further advantage associated with the disposable absorbent articles of the present invention (e.g., pantiliners or pads) comprising within the absorbent core a spore-forming antagonistic microorganism and/or the spores thereof (dormant form of the micro-organisms), is a better protection as well as better feeling and more acceptable cleanness level in use. Indeed, it has further been found that the spore forming microorganism and/or spores described herein, allow gelification of the bodily fluid discharge upon contact therewith, thereby facilitating fluid control into the article. Indeed the presence of the spore forming microorganisms and/or spores in the absorbent core of the absorbent article by changing the physical properties of the bodily fluid discharge enhances the fluid control properties of the article. Such gelification will have the benefits of retaining the bodily fluid within the absorbent core thereby reducing the rewetting of the topsheet and/or the soiling through as might otherwise result from squeezing the article for example as a consequence of legs movement of a person wearing the article.

Whereas the present invention is preferably directed to disposable articles like pantiliners, feminine napkins, incontinent pads, diapers, tampons, interlabial pads, perspiration pads, surgical pads, breast pads, human or animal waste management devices and the like, other articles may include the spores as described herein and/or micro-organisms too for the purpose of malodours control. Indeed, other applications include other articles designed to be worn in contact with the external surface of a human or an animal such as clothing, bandages, thermal pads, acne pads, cold pads, compresses, surgical pads/dressings and the like, body cleansing articles like impregnated wipes (e.g. baby wipes, wipes for feminine intimate hygiene), articles for absorbing perspiration such as shoe insoles, and articles for animals like litters and the like.

BRIEF DESCRIPTION OF THE DRAWINGS

The invention is further described with reference to the accompanying drawing.

Figure 1:
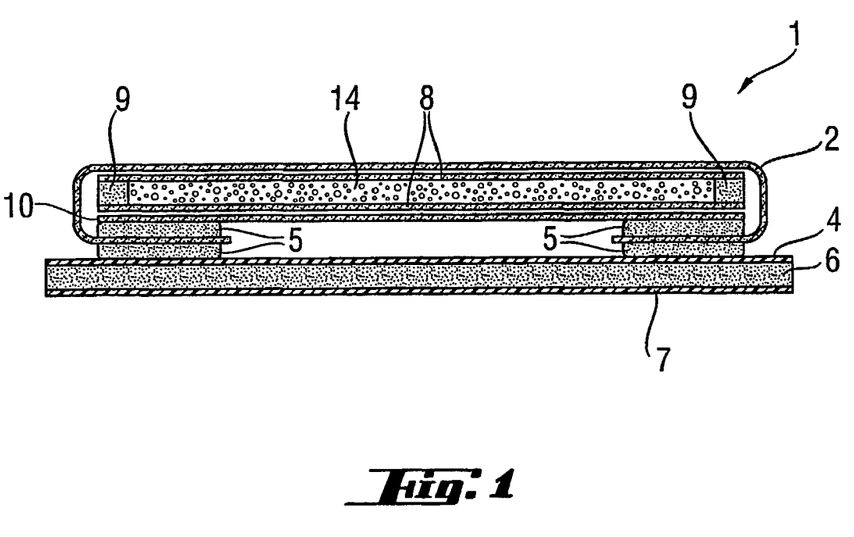
FIG. 1 shows a cross sectional view of a pantiliner having an absorbent core comprising three cellulose tissue layers, the spores being incorporated between the first and second tissue layers.

SUMMARY OF THE INVENTION

The present invention relates to a disposable absorbent article comprising an absorbent core comprising at least a spore which has the ability to germinate into a microorganism which exhibits antagonistic properties against undesirable strains of microorganisms, typically present or arisen in the article and/or at least a spore-forming microorganism exhibiting antagonistic properties against undesirable strains of micro-organisms The present invention also encompasses the use, in an article, preferably a disposable article, of spores which have the ability to germinate into microorganisms which exhibit antagonistic properties against undesirable strains of microorganisms, for effective odour control.

The present invention further encompasses the use, in an article, preferably a disposable article, of spores which have the ability to germinate into microorganisms which exhibit antagonistic properties against undesirable strains of microorganisms, for long lasting antagonistic properties under favourable condition, e.g., for long lasting odour control of the article in use (for instance when worn in the urogenital zone).

The present invention further encompasses the use, in an article, preferably a disposable absorbent article, of spore-forming microorganisms exhibiting antagonistic properties against undesirable strains of microorganisms, preferably *B. coagulans,* for long lasting antagonistic properties against undesirable strains of micro-organisms, typically for long lasting odour control of the article in use (for instance when worn in the urogenital zone).

The present invention yet encompasses the use, in an article, preferably disposable absorbent article, typically the absorbent core of the article, of spore-forming microorganisms exhibiting antagonistic properties against undesirable strains of microorganisms and/or spores thereof, preferably *B. coagulans,* for enhanced fluid control upon contact with fluid typically bodily fluid.

DETAILED DESCRIPTION OF THE INVENTION

In one aspect the present invention relates to articles particularly suitable for external application to a human or animal which comprise spores which have the ability to germinate into micro-organisms which exhibit antagonistic properties against undesirable strains of micro-organisms and/or spore forming microorganisms exhibiting antagonistic properties against undesirable strains of microorganisms.

By "article" it is meant herein any tridimentional solid material being able to receive/carry spores as described herein. By "article suitable for external application to a human or animal", it is meant any article suitable to be applied or worn in contact with the body of e.g., a human including especially the skin and the urogenital zone. Vaginal application (e.g., tampon) is considered external according to the present invention. The term 'disposable' is used herein to describe articles which are not intended to be launched or otherwise restored or reused as an article (i.e., they are intended to be discarded after a single use and, preferably to be recycled, composted or otherwise disposed of in an environmentally compatible manner).

Preferred articles according to the present invention are disposable absorbent articles that are designed to be placed against or in proximity to the body of a wearer and to absorb and/or contain fluids/exudates discharged from the body, such as pantiliners, sanitary napkins, catamenials, incontinence inserts/pads, diapers, tampons, interlabial pads/inserts, breast pads, human or animal waste management devices and the like. Typically such human urine or faecal management devices comprise a bag having an aperture and a flange surrounding the aperture for preferably adhesive attachment to the urogential area and/or the perianal area of a wearer. Any faecal or urine management device known in the art is suitable for use herein. Such devices are described in for example WO 99/00084 to WO 99/00092. Other articles suitable according to the present invention also include other articles designed to be worn in contact with the body such as clothing, bandages, thermal pads, acne pads, cold pads, compresses, surgical pads/dressings and the like, articles for absorbing perspiration such as shoe insoles, shirt inserts, perspiration pads and the like, body cleansing articles like impregnated wipes (e.g. baby wipes, wipes for feminine intimate hygiene), impregnated tissues, towels, and the like, and articles for animals like lifters and the like.

By "bodily fluids or discharges" it is meant herein any fluid produced by human or animal body occurring naturally or accidentally like for instance in the case of skin cutting, including for instance perspiration, urine, menstrual fluids, faeces, vaginal secretions and the like.

As an essential element the articles of the present invention comprise at least a spore which germinates in a microorganism which exhibits antagonistic properties against undesirable strains of microorganisms, typically present or arisen in the article and/or a spore forming micro-organism exhibiting antagonistic properties.

The spores also called endospores to be used herein are the dormant form of spore-forming micro-organisms (living form) which exhibit antagonistic properties against undesirable strains of micro-organisms. The use of the spores are preferred herein as they both provide stability benefits during use but also during storage (i.e. prior actual use of the articles).

The microorganisms to be used herein have the ability to survive in hostile environment in spore form (dormant form). Sporulation is the development in microorganisms of bodies each wrapped in a protective coat (a natural process of microencapsulation in a calcium-dipicolinic acid-peptidoglycan complex). Under favorable conditions, the spores germinate into viable bacilli (living form) and carry on their life activities.

These spores/endospores to be used herein are heat-resistant, dehydrated resting cells that are formed intracellularly and contain a genome and all essential metabolic machinery. The spores are encased in a complex protective spore coat.

Suitable spore-forming antagonistic microorganisms for use herein include the microorganisms combining the advantage of producing spores (also called endospores) which corresponds to the dormant form of the microorganisms together with the advantage of releasing antagonistic metabolites mainly lactic acid. Micro-organisms for use herein per se or which are able to form such spores for use herein belong to the genus Bacillus and are typically selected from the group consisting of *Bacillus coagulans* (also called *Lactobacillus sporogenes*), *Bacillus subtilis, Bacillus laterosporus* and *Bacillus laevolacticus.* Other microorganisms for use herein are those belonging to the genus *Sporolactobacillus*, more particularly the species Sporolactobacillus inulinus. Highly preferred herein is the species *B. coagulans* (also called *L. sporogenes*).

*L. sporogenes* was first isolated from green malt and described in 1933 by L. M. Horowitz-Wlassowa and N. W. Nowotelnow. It was submitted as *L. sporogenes* in the fifth edition (1939) of 'Bergey's manual of Determinative Bacteriology' as well as mentioned in recognized scientific publication, Korean J. Appl. Microb. & Bioengin. (1985) 13:185–190, J. Pharmaceut. Soc. Korea (1977) vol XXIII, Feb. 1, 473–474. *L. sporogenes* was transferred to *Bacillus coagulans* in the seventh edition of 'Bergey's manual of Determinative Bacteriology' due to simplification in cataloguing. However in honour of the original discoverers the name *L. sporogenes* is still used widely. Reference is also made to the taxonomical classification of Sporolactobacillus in L'integratore Nutrizionale 2 (1) 1999, Stabilita' di integratori con *Sporolactobacillus*, classificazione tassonomica by L. Marossi and all.

According to the Eighth Edition of Bergey's Manual of Determinative Bacteriology, "various spore-bearing rods which produce lactic acid, are facultative or aerobic and catalase positive, have generally and correctly been assigned to the genus *Bacillus*'. The characteristics of *B coagulans* as cited in 'Bergey's Manual of Determinative Bacteriology' (seventh edition) and other sources are "non pathogenic gram positive spore-forming bacteria (rods 0.9 by 3.0 to 5.0 micron size), aerobic to microaerophilic, producing L (+) lactic acid (dextrorotatory) in homofermentation conditions". *B coagulans* also releases other metabolites like carbon dioxide, diacetyl, bacteriocins, lacto-peroxidase. It has been isolated from natural sources, such as heat-treated soil samples inoculated into nutrient medium (Bergey's Manual of Systemic Bacteriology, Vol. 2, Sneath, P. H. A. et al., eds., Williams & Wilkins, Baltimore, Md., 1986).

Since *B. coagulans* (also called *L. Sporogenes*) exhibits characteristics typical of both genera *Lactobacillus* and *Bacillus*, its taxonomic position between the families Lactobacillaceae and Bacillaceae has often been discussed. This along with the fact that there is no universally accepted official classification leaves room for controversy in the nomenclature. More information about *L. sporogenes* (also called herein *B. Coagulans*) is available from the commercial brochure 69/107, incorporated herein by reference, of Sochim International s.p.a. Milano, a supplier of the spore form of *L. Sporogenes*.

There are a variety of different *bacillus* species, including, but not limited to many different strains available through commercial and public sources, such as the American Tissue Culture Collection (ATCC). As already said some authors refer to *Bacillus coagulans* as *L. sporogenes*. *Bacillus coagulans* Hammer deposited as *Lactobacillus sporogenes* by Kabushiki Kaisha Naruse Fermentation Research Laboratory is commercially available under ATCC number 31284 (Internet information source: http://www.atcc.org/). *Bacillus coagulans* strains are further available as ATCC Accession Numbers 15949, 8038, 35670, 11369, 23498, 51232, 11014, 12245, 10545 and 7050. *Bacillus subtilis* strains are available as ATCC Accession Numbers 10783, 15818, 15819, 27505, 13542, 15575, 33234, 9943, 6051a, 25369, 11838, 15811, 27370, 7003, 15563, 4944, 27689, 43223, 55033, 49822, 15561, 15562, 49760, 13933, 29056, 6537, 21359, 21360, 7067, 21394, 15244, 7060, 14593, 9799, 31002, 31003, 31004, 7480, 9858, 13407, 21554, 21555, 27328 and 31524. *Bacillus laterosporus* strains are available as ATCC Accession Numbers 6456, 6457, 29653, 9141, 533694, 31932 and 64, including *Bacillus laterosporus* BOD. *Bacillus laevolacticus* strains are available as ATCC Accession Numbers 23495, 23493, 23494, 23549 and 23492.

The spores for use herein are typically activated due to the presence of substrate, temperature increase and pH change. The optimum growth temperature range for the spores of *B. coagulans* is between 30° C. and 50° C. and the optimum pH range is from 5.0 to 6.5. Thus perspiration (pH 6) and fluid discharge like menstrual fluid discharge (pH 6.5), milk discharge (pH 6.4) and/or urine discharge (pH 6.4) will active the germination of the spores herein.

*B. coagulans* spores are ellipsoidal bodies measuring 0.9 to 1.2 by 1.0 to 1.7 microns. These spores are commercially available in a white to greyish powder form. *B. coagulans* (also called *L. sporogenes*) spores powder is commercially available under the name LACTOSPORE® from SABINSA CORPORATION (Sochim international s.p.a, Milano). 1 gram of LACTOSPORE® corresponds to $15*10^9$ spores and thus to $15*10^9$ cfu (colony forming unit) of *B. coagulans* (*L. sporogenes*).

It is necessary for the spores or microorganisms per se to be added in amounts which will achieve the desired effect under favorable conditions. Typically, such spores are present in the article herein at a level per article of more than $10^2$, preferably more than $10^4$, more preferably from $10^5$ to $10^{12}$, more preferably from $10^6$ to $10^{10}$ and most preferably from $10^7$ to $10^{12}$ cfu. This typically corresponds to a number of spore-forming microorganisms per article which exceeds $10^2$ cfu, preferably exceeds $10^4$ cfu, more preferably from $10^5$ cfu to $10^{12}$ cfu, even more preferably from $10^6$ to $10^{10}$ cfu and most preferably is from $10^7$ to $10^{12}$ cfu.

In the aspect of the invention wherein the spores are used, the articles according to the present invention can be stored for longer time period before actual use and still contain their whole antagonistic capacity up to the time the articles are used. Indeed *B. coagulans* cells (in spore form) are protected from destruction by environmental factors by the naturally-present microencapsulation system, the spore coat. These spores are activated by environmental changes like pH and temperature changes and availability of substrate. For instance in use when the article is contacted with the skin or the urogenital zone of a wearer, the temperature increases (from room temperature to above 30° C.–35° C.), substrates like humidity and bodily fluid discharge are provided and the pH will be stabilized between 5.0 to 6.5, such conditions will activate the spores germination. The spore coat imbibe water, swell and the increased water content will cause a rise in the metabolic rate of the sporulated bacili. Outgrowths will begin to protrude from the spore-coats. The outgrown cells germinate and transform into viable vegetative cell (also called 'living form' herein). The living form begin to proliferate multiplying rapidly. These living forms continue their metabolic activities producing lactic acid and other metabolites which render the environmental non-conducive for the growth of harmful pathogenic microorganisms. The germination process will be influenced by the body discharge in the article, leading to a somehow controlled germination process on demand. In other words all the spores will not germinate with the same kinetic but the germination will be in relation to the body fluid discharge on the article. This will contribute to further prolonging the effective beneficial microbial activity.

An important advantage of the spores used according to the present invention is that the spores can be stored at room temperature (20°–25° C.) without loss of viability as opposed to non-spore forming antagonistic bacteria like those taken from the genera *Lactobacillus* or *Lactococcus* like *Lactobacillus acidophilus, Lactococcus lactis* and the like.

In another aspect of the present invention the spore forming microorganisms are used. The spore-forming micro-organisms, especially *B coagulans,* have the ability to create very quickly an environment that is not suitable for the growth of pathogens. This is due to the rapid growth, high yield and reproducibility of such micro-organisms in comparison to other lactic acid producing bacteria like *Lactobacillus acidophilus.* For example *B coagulans* needs 30 minutes for one generation while *L. acidophilus* needs 80 minutes. Furthermore the particularity of these micro-organisms is that these microorganisms are spore forming antagonistic micro-organisms, i.e., they are able to survive longer and reproduce themselves in comparison to non spore-forming micro-organisms. Indeed in contrast to non-spore forming bacteria like *L. acidophilus, B coagulans* are transformed in spores (dormant form) when the substrate is reduced (in absence or reduced amount of bodily fluid discharge) and germinate again upon further bodily fluid discharge, i.e., reproduce themselves again through the spore form. In other words, by the formation of spores these micro-organisms can germinate and re-germinate in time sequence in line with the bodily fluid discharge (growth media) into an absorbent article, thereby ensuring long-lasting antagonistic properties against pathogens.

Indeed *B coagulans* cells (in spore form) are protected from destruction by environmental factors by the naturally-present microencapsulation system, the spore coat. Once in the spore form the microorganism has the ability to be reactivated by environmental changes like pH and temperature changes and availability of substrate, typically by further bodily fluid discharge. For instance in use when the article is contacted with the skin or the urogenital zone of a wearer, substrates like humidity, transpiration and/or bodily fluid discharge are provided upon different sequence of time and hence the spores germination cycle will be in line with availability of the substrates. The optimum growth temperature range for these spores is between 30° C. and 50° C. and the optimum pH range is from 5.0 to 6.5. New fluid discharge like perspiration (pH 6), menstrual fluid discharge (pH 6.5), milk discharge (pH 6.4) and/or urine discharge (pH 6.4) will active the germination/re-germination of the spores. The spore coat imbibe water, swell and the increased water content will cause a rise in the metabolic rate of the sporulated bacilli. Outgrowths will begin to protrude from the spore-coats. The outgrown cells germinate and transform into viable vegetative cell (the microorganism in its 'living form'). The living form begin to proliferate multiplying rapidly. These micro-organisms continue their metabolic activities producing lactic acid and other metabolites which render the environmental non-conducive for the growth of harmful pathogenic micro-organisms. The germination process will be influenced by the body discharge in the article, leading to a somehow controlled germination process on demand. In other words all the spores will not germinate with the same kinetic but the germination will be in relation to the body fluid discharge on the article. This will contribute to sustain the effective beneficial microbial activity.

Malodour is generated among other by inter or extra cellular metabolic activity which satisfy the bacteria needs for energy and proliferation. The metabolic activity aiming the production of vital oxygen, carbon and ammonium sources, leads to degraded odorous compounds as by products which are among low molecular weight of fatty acids, amines, mercaptan, indoles, ammonium, sulfides and the like. Bacteria that cause unpleasant smells may belong to, for example, the family Enterobacteriaceae, e.g., *Proteus mirabilis, Proteus vulgaris, Escheriachia coli* and *Klebsiella.*

The particularities of the spores used herein is based on the microbiological antagonism of their living form. The particularities of the spore forming microorganisms used herein is based on their antagonistic properties. Although not wishing to be bound by any particular theory, this implies that such antagonistic microorganisms inhibit other micro-organisms by competing for substrates, forming metabolites like L (+) form of lactic acid, enzymes like lacto-peroxidases, toxins, carbon dioxide, peroxides or antibiotics, so-called bacteriocines. The spores used herein upon activation and hence corresponding microorganisms have the ability to sustain their growth and reduce the patogenicity of many pathogens like ones mentioned herein before and especially *Proteus, Pseudomonas, Echerichia, Klebsiella, Enterococcus, Staphylococcus, Streptococcus* and *Candida.* In other words there is believed to be a competitive inhibition of growth of pathogens due to superior colonization of the antagonistic micro-organisms (also called probiotic microorgoanisms).

It is speculated that the production of lactic acid lowers the pH to 4–5, thereby inhibiting the growth of putrefactive organisms like *E. coli,* which require a higher optimum pH (typically 6 to 7) for favourable growth conditions. Furthermore undissociated lactic acid has the tendency to penetrate the membrane of pathogens, lowering their intracellular pH and/or interfering with their metabolic processes such as oxidative phosphorylation, thereby inhibiting the growth of such pathogens.

Other metabolites further contribute to inhibit the growth of pathogens. For example carbon dioxide is believed to reduce membrane permeability. Hydrogen peroxide/Lactoperoxidase are believed to oxidise basic proteins and to destroy the "enzymes factories" (ribosomes) of pathogens. Bacteriocins are proteins or protein complexes with bactericidal activity. Indeed, bacteriocins have the ability to link to particular receptors on the cell wall of microorganisms, thereby affecting the functionality of the cell wall/membranes. Bacteriocins are also able to affect DNA-synthesis and protein synthesis.

The particularity of the spores of the spore-forming microorganisms herein is that they germinate into antagonistic microorganisms that may be naturally occurring microorganisms that are non-toxic and do not have any negative biological effect on humans.

One advantage afforded by the use of such antagonistic microorganisms is that there is avoided an undesired selection pressure on the micro environment, such as favoring potential desease-promoting microorganisms and therewith the risk of developing pathogenic strains that are resistant to antibiotics and chemopharmaceutical preparations. Since the antimicrobial system is based on a natural, biological process, there is less risk of environmental ecological and toxic disturbances.

A further important advantage associated with the spores and/or microorganisms according to the present invention is that they also provide the disposable absorbent article into which they have been incorporated with a better protection, better feeling and more acceptable cleanness level. Indeed the viable form of the spores herein have the ability to gelify bodily fluid discharge in the article thereby retaining the discharge in its close proximity, i.e., in the core of the article wherein it is applied to. This results in a dry and clean topsheet as well as in reduced wet through.

Without to be bound by theory, it is speculated that the cause of this gelification is the denaturation of the proteins. Indeed the spores herein upon activation/germination in their living form and spore-forming microorganisms as described herein when used per se release lactic acid through glycogen fermentation. As proteins are sensitive to pH, the presence of lactic acid causes the soluble proteins contained into the bodily fluid to turn into insoluble form. This creates a sort of tri-dimensional net of molecules trapping globules, minerals, fats which results in the so called gelification of the bodily fluid and hence in control/retention of bodily fluids.

Advantageously the microorganisms herein are easily cultivated, have a rapid growth, high yield and are readily handled at technical handling thereof. Furthermore in contrast to non-spore forming microorganisms belong to the genera *Lactobacillus* and/or *Pediococcus* the microorganisms herein do not need continuous re-inoculation to maintain the microorganisms in a given media. Indeed they are able to re-inoculate themselves again through the spore form. These circumstances make the microorganisms herein also more easy to handle and thus also cheaper.

The microorganisms herein when used in living form are typically used in a freeze-drying form. Their isolation process follows known routine processes for the isolation of pure cultures. The isolated pure cultures are then typed according to known methods, e.g., API. The microorganisms as described herein are then cultivated in a fermentor in a manner known per se, are separated from the medium using a separator or a centrifuge, are freeze-dried in a manner known per se and ground to a fine powder. The bacterial concentrate in powder so obtained is then typically mixed with a fermentable carbohydrate, e.g., glucose, to a desired concentration. Typically a final concentration of about 100–150 billion viable microorganisms per gram is obtained. Such powder is then ready for use in the absorbent article. Alternatively in some case it is possible to add the living bacteria to the absorbent article and then carry out a freeze drying thereof. Another available form is a lyophilized form.

In one embodiment herein wherein the living form of the microorganisms are used, the articles, typical disposable absorbent articles might be dried to a moisture content of less than 10%, preferably less than 5% and most preferably less than 1%, calculated as percentage of weight of the article.

Growth of *B. Coagulans*

The growth of various bacillus species to form cell cultures, cell pastes and spore preparations is generally well known in the art. *B coagulans* growth described herein after can readily be used for the other bacillus species. *B. coagulans* is aerobic and facultative, it growths typically in nutrient broth, pH 5.7 to 6.8 containing up to 2% (by weight) NaCl, although neither NaCl nor KCl are required for growth. It is optimally grown at about 30° C. to 55° C. and the spores can withstand pasteurization. *B coagulans* can be grown in a variety of media, although it has been found that certain growth conditions produce a culture which yields a high level of sporulation. For example, sporulation is enhanced if the culture medium includes 10 milligrams per liter of manganese sulfate, yielding a ratio of spores (dormant form) to vegetative cells (living form) of about 80:20. In addition certain growth conditions produce a bacterial spore which contains a spectrum of metabolic enzymes particularly suited for the present invention, i.e. control of pathogen microorganisms generating malodour development. Although spores produced by these particular growth conditions are preferred, spores produced by any compatible growth conditions are suitable for producing a *B coagulans* useful in the present invention.

Suitable media for growth of *B coagulans* includes Nutristart 701, PDB (potato dextrose broth), TSB (tryptic soy broth) and NB (nutrient broth) all well known and available from a variety of sources. Media supplements containing enzymatic digests of poultry and fish tissue, and containing food yeast are particularly preferred. A preferred supplement produces a media containing at least 60% protein, and about complex carbohydrates and 6% lipids. Media can be obtained from a variety of commercials sources, notably DIFCO (Detroit Mich.), OXOID (Newark N.J.) BBL (Cockeyesville Md.) and Troy Biologicals (Troy Mich.).

A particularly suitable procedure for the preparation of *B. Coagulans* is as follows. *B coagulans* Hammer bacterium (e.g., ATCC# 31284) was inoculated and grown in nutrient broth containing 5 g Peptone, 3 g Meat extract, 10–30 mg $MnSO_4$ and 1000 ml distilled water adjusted to pH 7.0, using a standard airlift fermentation vessel at 30° C. The range of $MnSO_4$ acceptable for sporulation is 1 mg/l to 1 g/l. The vegetative cells can be actively reproduce up to 65° C. and the spores are stable up to 90° C. After fermentation, the *B coagulans* Hammer bacterial cells are collected using standard methods (e.g., filtration, centrifugation) and the collected cells and spores can be lyophilized, spray dried, air dried or frozen. As described herein, the supernatant from the cell culture can be collected and used as an extracellular agent secreted by *B coagulans* which has antimicrobial activity useful in a formulation of this invention. A typical yield from the above culture is about 100 to 150 billion cells/spores per gram before drying. Spores maintain at least 90% viability after drying-when stored at room-temperature for up to seven years, and thus the effective shelf life of a composition containing *B coagulans* Hammer spores at room temperature is about 10 years.

Sources of *B Coagulans*

Purified *B coagulans* bacterium are available from the American type Culture Collection (Rockville, Md.) using the following accession numbers: *B coagulans* Hammer NRS T27 (ATCC# 11014), *B coagulans* Hammer strain C (ATCC# 11369), *B coagulans* Hammer (ATCC # 31284) and *B coagulans* Hammer NCA 4259 (ATCC# 15949). Purified *B coagulans* bacterium are also available from the Deutsche Sammlung con Miroorganismen und Zellkuturen GmbH (Braunschweig, Germany) using the following accession numbers: *B coagulans* Hammer $1915^{AL}$ (DSM#2356), *B coagulans* Hammer $1915^{AL}$ (DSM#2383, corresponds to ATCC#11014), *B coagulans* $Hammer^{AL}$ (DSM#2384, corresponds to ATCC#11369) and *B coagulans* $Hammer^{AL}$ (DSM#2385, corresponds to ATCC# 15949). *B coagulans* Bacterium can also be obtained from commercial suppliers such as Sabinsa Corporation (Piscataway,N.J.) Sochim International s.p.a. (Milano, Italy).

These *B coagulans* strains and their growth requirements have been described previously (Baker et al, Can.J.Microbiol. 6:557–563, 1960, Blumenstock, "*Bacillus coagulans* Hammer 1915 und andere thermophile oder mesophile, sauretolerante *bacillus*-Arten-eine taxonomische Untersuchung' Doctoral thesis, Univ. Goffingen, 1984, Nakamura et al, Int. J. Syst. Bacteriol, 38:63–73, 1988). Strains of *B coagulans* can also be isolated from natural sources (e.g., heat-treated soil samples) using well known procedures (Bergey's Manual of Systemic Bacteriology, Vol. 2, p. 1117, Sneath, P. H. A. et al, eds, Williams &Wilkins, Baltimore, Md., 1986).

Further description of Bacillus species of interest, namely *B coagulans* and properties thereof can be found in WO 98/47374 to Ganeden Biotech. Inc, incorporated herein by references.

Optional Agents

The articles according to the present invention may further comprise on top of the spores described herein before and/or micro-organisms described herein before, other conventional agents or mixtures thereof.

Absorbent Gelling Materials

As is well-known from recent commercial practice, absorbent gelling materials (sometimes referred to as "supersorbers") are becoming broadly used in absorbent articles. AGM's are materials which have fluid-absorbing properties.

Such materials are highly preferred herein due to their dual function of absorbing fluids and odors.

Such materials form hydrogels on contact with water (e.g., with urine, blood, and the like). One highly preferred type of hydrogel-forming, absorbent gelling material is based on polyacids, especially polyacrylic acid. Hydrogel-forming polymeric materials of this type are those which, upon contact with fluids (i.e., liquids) such as water or body fluids, imbibe such fluids and thereby form hydrogels. These preferred absorbent gelling materials will generally comprise substantially water-insoluble, slightly cross-linked, partially neutralized, hydrogel-forming polymer materials prepared from polymerizable, unsaturated, acid-containing monomers. In such materials, the polymeric component formed from unsaturated, acid-containing monomers may comprise the entire gelling agent or may be grafted onto other types of polymer moieties such as starch or cellulose. Acrylic acid grafted starch materials are of this latter type. Thus, the preferred absorbent gelling materials include hydrolyzed acrylonitrile grafted starch, acrylic acid grafted starch, polyacrylates, maleic anhydride-based copolymers and combinations thereof. Especially preferred absorbent gelling materials are the polyacrylates and acrylic acid grafted starch.

Whatever the nature of the polymer components of the preferred absorbent gelling materials, such materials will in general be slightly cross-linked. Crosslinking serves to render these preferred hydrogel-forming absorbent materials substantially water-insoluble, and cross-linking also in part determines the gel volume and extractable polymer characteristics of the hydrogels formed therefrom. Suitable cross-linking agents are well known in the art and include, for example, (1) compounds having at least two polymerizable double bonds; (2) compounds having at least one polymerizable double bond and at least one functional group reactive with the acid-containing monomer material; (3) compounds having at least two functional groups reactive with the acid-containing monomer materials; and (4) polyvalent metal compounds which can from ionic cross-linkages. Cross-linking agents of the foregoing types are described in greater detail in Masuda et al; U.S. Pat. No. 4,076,663; Issued Feb. 28, 1978. Preferred cross-linking agents are the di- or polyesters of unsaturated mono-or polycarboxylic acids with polyols, the bisacrylamides and the di-or triallyl amines. Especially preferred cross-linking agents are N,N'-methylenebisacrylamide, trimethylol propane triacrylate and triallyl amine. The cross-linking agent will generally comprise from about 0.001 mole percent to 5 mole percent of the preferred materials. More preferably, the cross-linking agent will comprise from about 0.01 mole percent to 3 mole percent of the gelling materials used herein.

The preferred, slightly cross-linked, hydrogel-forming absorbent gelling materials will generally be employed in their partially neutralized form. For purposes described herein, such materials are considered partially neutralized when at least 25 mole percent, and preferably at least 50 mole percent of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to as the "degree of neutralization". Typically, commercial absorbent gelling materials have a degree of neutralization somewhat less than 90%.

The preferred absorbent gelling materials used herein are those which have a relatively high capacity for imbibing fluids encountered in the absorbent articles; this capacity can be quantified by referencing the "gel volume" of said absorbent gelling materials. Gel volume can be defined in terms of the amount of synthetic urine absorbed by any given absorbent gelling agent buffer and is specified as grams of synthetic urine per gram of gelling agent.

Gel volume in synthetic urine (see Brandt, et al, below) can be determined by forming a suspension of about 0.1–0.2 parts of dried absorbent gelling material to be tested with about 20 parts of synthetic urine. This suspension is maintained at ambient temperature under gentle stirring for about 1 hour so that swelling equilibrium is attained. The gel volume (grams of synthetic urine per gram of absorbent gelling material) is then calculated from the weight fraction of the gelling agent in the suspension and the ratio of the liquid volume excluded from the formed hydrogel to the total volume of the suspension. The preferred absorbent gelling materials useful in this invention will have a gel volume of from about 20 to 70 grams, more preferably from about 30 to 60 grams, of synthetic urine per gram of absorbent gelling material.

Another feature of the most highly preferred absorbent gelling materials relates to the level of extractable polymer material present in said materials. Extractable polymer levels can be determined by contacting a sample of preferred absorbent gelling material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. The particular procedure used to determine extractable polymer content of the preferred absorbent gelling agent buffers herein is set forth in Brandt, Goldman and Inglin; U.S. Pat. No. 4,654,039; Issues Mar. 31, 1987, Reissue No. 32,649, The absorbent gelling materials which are especially useful in the absorbent articles herein are those which have an equilibrium extractables content in synthetic urine of no more than about 17%, preferably no more than about 10% by weight of the absorbent gelling material.

The absorbent gelling materials herein before described are typically used in the form of discrete particles. Such absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of absorbent gelling material particles may also be used.

The size of the absorbent gelling material particles may vary over a wide range. For reason of industrial hygiene, average particle sizes smaller than about 30 microns are less desirable. Particles having a smallest dimension larger than about 2 mm may also cause a feeling of grittyness in the absorbent article, which is undesirable from a consumer aesthetics standpoint. Furthermore, rate of fluid absorption can be affected by particle size. Larger particles have very much reduced rates of absorption. Preferred for use herein are absorbent gelling material s particles substantially all of which have a particle size of from about 30 microns to about 2 mm. "Particle Size" as used herein means the weighted average of the smallest dimension of the individual particles.

Highly preferred absorbent gelling materials for use herein are partially neutralized absorbent gelling material (i.e., at least 25 mole percent of monomers used to form the polymer are acid group-containing monomers which have been neutralized with a salt forming cation). Indeed it has been found that the addition of absorbent gelling materials, especially partially neutralised absorbent gelling materials (e.g., cross linked sodium polyacrylate with a degree of neutralization of about 70% and pH of about 5.7 to 6.3 as XZ9589001 from Dow Chemicals) on top of the lactic acid producing microorganisms described herein in a disposable article according to the present invention (especially the absorbent core thereof) results in further reduction of undesirable odours associated with bodily discharge occurrence in the article during use conditions. Without to be bound by any theory it is speculated that the absorbent gelling material, especially when partially neutralised, acts as a pH regulating substance (pH buffering agent), regulating the pH in a range from 4.5 to 6.8, preferably from 5 to 6.5), which is beneficial with respect to the inhibition of the growth of undesirable bacteria and therewith the occurrence of undesirable odours.

Typically, the amount of absorbent gelling material particles used in the articles herein, preferably the disposable absorbent articles, will range from 0 $gm^{-2}$ to 150 $gm^{-2}$, preferably from 30 $gm^{-2}$ to 110 $gm^{-2}$, more preferably from 55 $gm^{-2}$ to 85 $gm^{-2}$.

Odour Control Agents

For instance additional odour control agent or combinations thereof, known in the art for this purpose may be used herein. These agents can typically be classified according to the type of odour the agent is intended to combat. Odors may be chemically classified as being acidic, basic or neutral.

Alternatively, the odor control agents may be categorised with respect to the mechanism by which the malodor detection is reduced or prevented. For example, odor control agents which chemically react with malodorous compounds or with compounds which produce malodorous degradation products thereby generating compounds lacking odor or having an odor acceptable to consumers may also be utilized herein.

Suitable odor control agents for use herein typically include carbonates (e.g., sodium carbonate), bicarbonates (e.g., sodium bicarbonate), phosphates (e.g., sodium phosphate), sulphates (e.g., zinc and copper sulphates), carboxylic acids such as citric acid, lauric acid, boric acid, adipic acid and maleic acid, activated carbons, clays, zeolites, silicas and starches. Such odor control agents and systems are disclosed in more details hereinafter and for example in EP-A-348 978, EP-A-510 619, WO 91/12029, WO 91/11977, WO 91/12030, WO 81/01643 and WO 96/06589. Alternative odor control agents are ion exchange resins such as those described in U.S. Pat. No. 4,289,513 and U.S. Pat. No. 3,340,875. Masking agents such as perfumes may also be used as odor control agents herein.

Typically, the articles like disposable absorbent articles may comprise the odour control agent or a mixture thereof at a level of from 0 $gm^{-2}$ to 600 $gm^{-2}$, preferably from 5 to 500 $gm^{-2}$, more preferably from 10 $gm^{-2}$ to 350 $gm^{-2}$ and most preferably from 20 $gm^{-2}$ to 200 $gm^{-2}$ Preferred odour control agents for use herein are the odour absorbing agent or a mixture thereof. Indeed in a broadest aspect the present invention is based on a synergistic odour reduction by combining them with the microorganisms/spores as described herein. Suitable odour absorbing agents for use for this purpose include activated carbons, clays, zeolites, silicas, kieselguhr, starches, cyclodextrin, ion exchange resins and the like. Preferred herein are silicas and/or zeolites. Highly preferred herein is a mixture of silica and zeolite.

Cyclodextrin and derivatives thereof may be used as described in U.S. Pat. No. 5,429,628. Ion exchange resins may be used such as those described in U.S. Pat. No. 4,289,513 and U.S. Pat. No. 3,340,875.

Silica

Particularly suitable herein as an odor absorbing agent is silica. Silica, i.e. silicon dioxide $SiO_2$ exists in a variety of crystalline forms and amorphous modifications, any of which are suitable for use herein. In particular, silicas having a high surface area or in agglomerated form are preferred. Silica molecular sieves are not considered to be within the definition of silica as used herein. Preferably the silica is in a highly purified form such that is contains at least 90%, preferably 95%, more preferably 99% silicon dioxide. Most preferably the silica is silica gel having a 100% silica content. Alternatively, the silica may be provided from other sources such as metal silicates including sodium silicate.

Zeolite

Another particularly suitable odour absorbing agent herein is zeolite. The use and manufacture of zeolite material is well know in the literature and is described in the following reference texts: ZEOLITE SYNTHESIS, ACS Symposium Series 398, Eds. M. L. Occelli and H. E Robson (1989) pages 2–7; ZEOLITE MOLECULAR SIEVES, Structure, Chemistry and Use, by D. W. Breck, John Wiley and Sons (1974) pages 245–250, 313–314 and 348–352; MODERN APPLICATIONS OF MOLECULAR SIEVE ZEOLITES, Ph.D. Dissertation of S. M. Kuznicki, U. of Utah (1980), available from University of Microfilms International, Ann Arbor, Mich., pages 2–8.

Zeolites are crystalline aluminosilicates of group IA and group IIA elements such as Na, K, Mn, Ca and are chemically represented by the empirical formula:

where y is 2 or greater, n is the cation valence, and w is the water content in the voids of the zeolite.

Structurally, zeolites are complex, crystalline inorganic polymers based on an infinitely extending framework of $AlO_4$ and $SiO_4$ tetrahedra linked to each other by sharing of oxygen ions. This framework structure contains channels or interconnected voids that are occupied by the cations and water molecules.

The structural formula of a zeolite is based on the crystal unit cell, the smallest unit of structure, represented by $$M_{x/n}[(AlO_2)_x(SiO_2)_y] \cdot wH_2O$$

where n is the valence of cation M, w is the number of water molecules per unit cell, x and y are the total number of tedrahedra per unit cell, y/x usually having values of 1–5.

Zeolites may be naturally derived or synthetically manufactured. The synthetic zeolites being preferred for use herein. Suitable zeolites for use herein include zeolite A, zeolite P, zeolite Y, zeolite X, zeolite DAY, zeolite ZSM-5, or mixtures thereof. Most preferred is zeolite A.

According to the present invention the zeolite is preferably hydrophobic. This is typically achieved by increasing the molar ratio of the $SiO_2$ to $AlO_2$ content such that the ratio of x to y is at least 1, preferably from 1 to 500, most preferably from 1 to 6.

In a preferred embodiment herein the article comprises silica together with zeolite as the odour absorbing agents in a weight ratio of silica to zeolite in a range of from 1:5 to 5:1, preferably from 3:1 to 1:3 and most preferably about 1:1.

Carbon Material

The carbon material suitable for employment herein is the material well known in the art as an absorber for organic molecules and/or air purification purposes. Carbon suitable for use herein is available form a number of commercial sources under the trade names such as CALGON Type "CPG", Type SGL, Type "CAL" and type "OL". Often such material is referred to as "activated" carbon or "activated" charcoal. Typically it is available in the form of an extremely fine, dusty particles having large surface areas (200—several thousand $m^2/g$.) It is to be understood that any of the "air purifying" or !"activated" carbons of commerce can be used in the practice of this invention.

The Disposable Articles

The spores and/or micro-organisms described herein before (and optional absorbing gelling material and/or optional additional odor control agent(s)) may be incorporated into a disposable article, preferably pantiliners, feminine napkins, incontinent pads, diapers, nursing pads, and the like by any of the methods disclosed in the art, for example layered on the core of the absorbent article or mixed within the fibres of the absorbent core.

The spores and/or micro-organisms as described herein and optional additional agents are preferably incorporated between two layers of cellulose tissue. Optionally the system may be bonded between two cellulose tissue layers with, for example, a hot melt adhesive or any suitable bonding system, as described in WO 94/01069.

In one embodiment of the present invention the spores and/or microorganisms as described herein and optional additional agents are incorporated in a layered structure in accordance with the disclosure of WO 94/01069 or WO 95/17868. WO 95/17868 describes a layered structure substantially as described in WO 94/01069 with the exception that WO 95/17868 comprises a much higher quantity of absorbent gelling material in the intermediate layer which is between the fibrous layers (at least 120 $gm^{-2}$) that would be incorporated as an optional component in the present invention. The intermediate layer comprises in particular a polyethylene powder as thermoplastic material which is mixed with the spore powder. The mixture is then heated such that the polyethylene melts and glues the laminate layers together.

Alternatively, the polyethylene powder may be replaced by a conventional glue for instance those commercially available from ATO Findley under the name H20-31® to glue the laminate layers and/or components together. Advantageously this method step allows to avoid the heating step necessary when using polyethylene powder. This might be typically used herein in the embodiment wherein the microorganism (living form) is used.

Adhesive lines are preferably also placed on the edges of the laminate to ensure that the edges of the laminate stick and any loose components present do not fall out of the laminate.

The spores and/or microorganisms described herein may be distributed homogeneously or non homogeneously in the absorbent core. The spores and/or microorganisms described herein may be distributed homogeneously or non homogeneously on the whole surface of the desired layer or layers, or on one or several area of the surface layer/layers to which it is positioned (e.g. central area and/or surrounding area like the edges of a layer of the absorbent core) or mixtures thereof. The presence of the spores and/or microorganisms described herein in the core (also called intermediate layer which is positioned between the topsheet and the backsheet) is preferred because the core collects, absorbs and stores/retains bodily fluids. Thus the close proximity to the substrate (i.e. bodily fluid) contributes to improved fluid control as well as to improved odour control. Indeed optimum inhibition of the degradation activity by putrefactive bacteria and proliferation of pathogens is obtained due to close proximity to the majority of the amount of bodily fluid present in a given disposable article with the spores and/or micro-organisms as described herein.

In one embodiment of the present invention the spores and/or microorganisms as described herein are used either together with odor control agent and/or absorbent gelling materials, they are positioned such that at least a portion of the fluid discharge comes into contact with said spores/microorganisms before the optional absorbent gelling material (e.g., AGM) and/or optional additional odour control agent if present. In particular, the spores can be located in a separate layer from the optional absorbing gelling material and/or optional additional odor control agent if present. In such an embodiment the spores/microorganisms are located towards the topsheet or in the topsheet itself (preferably the secondary topsheet) and the optional absorbing gelling material and/or optional additional odour control agent are located further away from the topsheet than the spores/microorganisms. The benefits of this execution are related with the fact that the inhibitory action by spores/microorganisms described herein starts immediately after the contact with body fluids and continue in the fluids storage layer. In this way pathogens microorganisms causing malodor have lower possibility and time to degrade body fluids already colonized by spores/microorganism as described herein typically B. coagulans.

The spores/microorganisms (freeze-dried form or lyophilized form for the microorganisms) may be incorporated as a powder or a granulate. When used in a granulate or particulate form the spores/microorganisms as described herein and the optional absorbing gelling material and/or optional odor control agent may be granulated separately and then mixed together or granulated together.

The preferred absorbent articles according to the present invention are described as follows:

Absorbent Core

According to the present invention, the absorbent can include the following components: (a) an optional primary fluid distribution layer preferably together with a secondary optional fluid distribution layer; (b) a fluid storage layer; (c) an optional fibrous ("dusting") layer underlying the storage layer; and (d) other optional components. According to the present invention the absorbent may have any thickness depending on the end use envisioned.

A Primary/Secondary Fluid Distribution Layer

One optional component of the absorbent according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilized. The fluid distribution layers can be comprised of any material typical for such distribution layers. In particular fibrous layers maintain the capillaries between fibers even when wet are useful as distribution layers.

B Fluid Storage Layer

Positioned in fluid communication with, and typically underlying the primary or secondary distribution layers, is a fluid storage layer. The fluid storage layer can comprise any usual absorbent material or combinations thereof. It preferably comprises absorbent gelling materials in combination with suitable carriers.

Suitable carriers include materials which are conventionally utilized in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins and panty liners.

An embodiment of the absorbent structure made according to the present invention may comprise multiple layers comprises a double layer tissue laminate formed by folding the tissue onto itself. These layers can be joined to each other for example by adhesive or by mechanical interlocking or by hydrogen bridge bands. Absorbent gelling material or other optional material can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the absorbent gelling material is dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing absorbent gelling materials partially or fully.

C Optional Fibrous ("Dusting") Layer

An optional component for inclusion in the absorbent core according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

D Other Optional Components of the Absorbent Structure

The absorbent core according to the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

The Topsheet

According to the present invention the absorbent article comprises as an essential component a topsheet. The topsheet may comprise a single layer or a multiplicity of layers. In a preferred embodiment the topsheet comprises a first layer which provides the user facing surface of the topsheet and a second layer between the first layer and the absorbent structure/core.

The topsheet as a whole and hence each layer individually needs to be compliant, soft feeling, and non-irritating to the wearer's skin. It also can have elastic characteristics allowing it to be stretched in one or two directions. According to the present invention the topsheet may be formed from any of the materials available for this purpose and known in the art, such as woven and non woven fabrics and films. In a preferred embodiment of the present invention at least one of the layers, preferably the upper layer, of the topsheet comprises a hydrophobic, liquid permeable apertured polymeric film. Preferably, the upper layer is provided by a film material having apertures which are provided to facilitate liquid transport from the wearer facing surface towards the absorbent structure. If present the lower layer preferably comprises a non woven layer, an apertured formed film or an airlaid tissue.

The Backsheet

The backsheet primarily prevents the extrudes absorbed and contained in the absorbent structure from wetting articles that contact the absorbent product such as underpants, pants, pyjamas and undergarments. The backsheet is preferably impervious to liquids (e.g. menses and/or urine) and is preferably manufactured from a thin plastic film, although other flexible liquid impervious materials can also be used. As used herein, the term "flexible" refers to materials that are compliant and will readily conform to the general shape and contours of the human body. The backsheet also can have elastic characteristics allowing it to stretch in one or two directions.

The backsheet typically extends across the whole of the absorbent structure and can extend into and form part of or all of the preferred sideflaps, side wrapping elements or wings.

The backsheet can comprise a woven or nonwoven material, polymeric films such as thermoplastic films of polyethylene or polypropylene, or composite materials such as a film-coated nonwoven material. Preferably, the backsheet is a polyethylene film typically having a thickness of from about 0.012 mm (0.5 mil) to about 0.051 mm (2.0 mil).

Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matt finished to provide a more clothlike appearance. Further, the backsheet can permit vapors to escape from the absorbent structure, i.e. be breathable, while still preventing extrudates from passing through the backsheet. Also breathable backsheets comprising several layers, e.g. film plus non-woven structures, can be used.

Odor Control Test

The odor reduction is measured by for example an in vitro sniff test. In vitro sniff test consists in analyzing by expert graders the odor associated with articles comprising the ingredients to be tested (including references articles) when contacted with an odourous components-containing solution.

The expert graders express their judgment about (un)pleasantness of the odor using a (un)pleasantness scale, typically from −10 (highest level of unpleasantness) to 5 (most pleasant). With this procedure, each grader compares MU (Unpleasantness) in the test session. The relative MU odor values from different products are assigned numbers. For example, in a test session, a sample that is perceived to be twice as strong as another is assigned twice as large a number. One that is perceived to be one-tenth as strong as another is assigned a number one-tenth as large, etc. In each test session, zero is used to designate neutral hedonicity, and + and − numbers are assigned in ratio proportion to the relative pleasantness and unpleasantness of the odor.

Surprisingly in vitro in-house sniff tests conducted by using an odourous components-containing solution reproducing the essential malodorous characteristics of menses showed synergistic odor reduction when spores/microorganisms as described herein (e.g. B coagulans) together with odour absorbing agent (e.g., silicate available as Syloblanc 82 from Grace GmbH and/or zeolite available as Zeolite A, Wessalith CSfrom Degussa AG) to each of these ingredients taken alone at the same total level of active. Indeed the % of unpleasantness reduction obtained for the mixture was higher than the % of unpleasantness reduction obtained for each of the two ingredients used alone at the same total level of active. The Unpleasantness values, for each sample, was obtained as a mean of at least 15 observations (3 products, 5 graders). These results were statistically significant.

Alternatively the odor reduction can also be measured with in vivo sniff tests as described in patent applications, EP-A-81 1387 or WO97/46191, herein incorporated by reference.

The present invention is further illustrated by the following example.

EXAMPLES

Example A

The feminine pads used in the following examples were Always (Always is a registered Trade Mark) as sold by the Procter & Gamble Company.

Each feminine pad was opened by cutting the wrap around the perforated coverstock at its bottom face approximately along a longitudinal edge of the release paper which covers the external adhesive layer. The side of the absorbent fibrous core was then exposed by slightly shifting the water impermeable plastic bottom layer and subsequently, the fibrous core was split into two halves, each having approximately the same thickness, along a plane which is parallel to the plane of the pad itself. *B. coagulans* spores powder was homogeneously distributed between these tow fibrous layers which were then joined together to reconstitute the absorbent core.

The water impermeable inner backsheet was then put back into its original position and the wrap around perforated coverstock was sealed along the cut by means of e.g. a double sided adhesive tape.

Samples were produced using the method above. *B. coagulans* spores powder used was Lactospore® (0.7 g) commercially available from Sabinsa Corporation (Sochim International S.P.A. Milano). 0.7 g of Lactospore® corresponds to about $10.5*10^9$ spores per pad (ten billions of spores per pad), i. e., about $10.5*10^9$ cfu of microorganisms per pad.

Example B

Other pads were prepared by following the method in Example A except that absorbing gelling material (AGM) was added on top of the *B. coagulans* spores in Example A. Accordingly *B. coagulans* spores and AGM were homogeneously distributed between these two fibrous layers which were then joined together to reconstitute the absorbent core.

*B. coagulans* spores powder used was Lactospore® (0.7 g) commercially available from Sabinsa Corporation (Sochim International S.P.A. Milano). The AGM (0.8 g) used was cross linked sodium polyacrylate XZ 9589001, available from Dow Chemicals.

Example C

Other pads were prepared by following the method in Example B except that after having split the fibrous core into two halves, the *B. coagulans* spores were homogeneously distributed onto the upper halve fibrous layer (i.e., the fibrous layer halve intended to be closer to the topsheet) and the AGM was homogeneously distributed onto the lower halve fibrous layer (i.e., the one intended to be closer to the backsheet of the pad once reconstituted). Then a layer of airlaid tissue (19 mm*70 mm of low basis weight) available from Fripa under the code/name NCB Tissue HWS was positioned between the two halve fibrous layers which are then joined together to reconstitute the absorbent core. The presence of the airlaid tissue between the two fibrous layer avoids direct contact between the *B. coagulans* spores and the AGM.

These samples were produced using as the *B. coagulans* spores Lactospore® (0.7 g) commercially available from Sabinsa Corporation (Sochim International S.P.A. Milano) and AGM (0.8 g) available from Dow Chemicals (XZ 9589001).

Example D

The pantiliners used in the following examples were Always pantiliners (Always is a Registered Trade Mark) as sold by the Procter & Gamble Company.

Each pantiliner was opened by cutting the polyethylene (PE) perforated film along a longitudinal edge of the pantiliner at its bottom face. The upper two layers of the inner three-folded cellulose tissue sheet, which constitutes the absorbent core of the pantiliner, were cut away and substituted with two layers of cellulose air laid tissue. *B. coagulans* powder was homogeneously dispersed between said two layers. The whole pantiliner structure was then reconstituted and sealed along the edges by means of adhesive.

FIG. 1 represents a sectional view of the pantiliner structure 1 which comprises a topsheet 2, airlaid layers 8 joined at their longitudinal edges with adhesive lines 9, *L sporogenes* powder 14, a tissue layer 10, a backsheet 4, adhesive area 5, an adhesive layer 6 and a removable release liner 7. Indeed FIG. 1 shows an absorbent core comprised of two layers of air laid cellulose tissue 8 joined at their longitudinal edges with adhesive 9 and having a layer of cellulose tissue 10 therebeneath to form a three layered absorbent core.

Samples were prepared by the method as described above, which samples incorporate *B. coagulans* spores as Lactospore® (0.7 g) commercially available from Sabinsa Corporation (Sochim International S.P.A. Milano). 0.7 g of Lactospore® corresponds to about $10.5*10^9$ spores per pantiliner (ten billions of spores per pad), i.e., about $10.5*10^9$ cfu of microorganisms per pantiliner.

Example E

Other pantiliners were prepared by following the method in Example D except that absorbing gelling material (AGM) was added on top of *B. coagulans* spores in Example D. Accordingly *B. coagulans* spores and AGM were homogeneously distributed between these two air laid layers which were then joined together to reconstitute the absorbent core.

*B. coagulans* spores powder used was Lactospore® (0.7 g) commercially available from Sabinsa Corporation (Sochim International S.P.A. Milano). The AGM (0.8 g) used was cross linked sodium polyacrylate XZ 9589001, available from Dow Chemicals.

Example F

The feminine pads used in the following examples were Always (Always is a registered Trade Mark) as sold by the Procter & Gamble Company.

Each feminine pad was opened by cutting the wrap around the perforated coverstock at its bottom face approximately along a longitudinal edge of the release paper which covers the external adhesive layer. The side of the absorbent fibrous core was then exposed by slightly shifting the water impermeable plastic bottom layer and subsequently, the fibrous core was split into two halves, each having approximately the same thickness, along a plane which is parallel to the plane of the napkin itself. *B Coagulans* powder was homogeneously distributed between these tow fibrous layers which were then joined together to reconstitute the absorbent core.

The water impermeable inner backsheet was then put back into its original position and the wrap around perforated coverstock was sealed along the cut by means of e.g. a double sided adhesive tape.

Samples were produced using the method above. *B Coagulans* powder used was freeze/dried commercially available under ATCC number 31284 (ATCC=American Type Culture Collection). Each pad contained about $10*10^9$ cfu of such microorganisms (ten billions cfu).

Example G

Other pads were prepared by following the method in Example F except that absorbing gelling material (AGM) was added on top of *B Coagulans* in Example F. Accordingly the *B Coagulans* and AGM were homogeneously distributed between these two fibrous layers which were then joined together to reconstitute the absorbent core.

*B Coagulans* powder used was freeze-dried powder commercially available under ATCC number 31284 (ATCC=American Type Culture Collection). Each pad contained about $10*10^9$ cfu of such micro-organisms. The AGM (0.8 g) used was cross linked sodium polyacrylate XZ 9589001, available from Dow Chemicals.

Example H

Other pads were prepared by following the method in Example G except that after having split the fibrous core into two halves, *B Coagulans* powder was homogeneously distributed onto the upper halve fibrous layer (i.e., the fibrous layer halve intended to be closer to the topsheet) and AGM was homogeneously distributed onto the lower halve fibrous layer (i.e., the one intended to be closer to the backsheet of the pad once reconstituted). Then a layer of airlaid tissue (19 mm*70 mm of low basis weight) available from Fripa under the code/name NCB Tissue HWS was positioned between the two halve fibrous layers which are then joined together to reconstitute the absorbent core. The presence of the airlaid tissue between the two fibrous layer avoids direct contact between *B Coagulans* and AGM.

These samples were produced using freeze-dried powder of *B Coagulans* commercially available under ATCC number 31284 (ATCC=American Type Culture Collection). The pads contained about $10*10^9$ of such microorganisms.

Example I

The feminine pads used in the following examples were Always (Always is a registered Trade Mark) as sold by the Procter & Gamble Company.

Each feminine pad was opened by cutting the wrap around the perforated coverstock at its bottom face approximately along a longitudinal edge of the release paper which covers the external adhesive layer. The side of the absorbent fibrous core was then exposed by slightly shifting the water impermeable plastic bottom layer and subsequently, the fibrous core was split into two halves, each having approximately the same thickness, along a plane which is parallel to the plane of the napkin itself. The odor adsorbing agents (Silica or Zeolite or both) were homogeneously mixed together with *B coagulans* powder and homogeneously distributed on this layer. Then all the layers were joined together to reconstitute the absorbent core.

The water impermeable inner backsheet was then put back into its original position and the wrap around perforated coverstock was sealed along the cut by means of e.g. a double sided adhesive tape.

*B. coagulans* spores powder commercially available as Lactospore® (0.7 g) from Sabinsa Corporation (Sochim International S.P.A. Milano). Thus each pad comprised about $10*10^9$ cfu of *L. sporogenes.* The silica (1 g) used was Syloblanc 82 available from Grace GmbH. The zeolite (0.8 g) used was Zeolite A, Wessalith CS, available from Degussa AG.

Alternatively other samples were prepared with *B. coagulans* (living form) commercially available under ATCC number 31284 in freeze-dried form instead of Lactospore®, the samples comprising about $10^9$ cfu of such microorganisms.

Example J

In Example J samples were produced using the same method as in Example I, except that AGM (0.8 g) available from Dow Chemicals (XZ 9589001), was added to *B coagulans* and odor absorbing agents (silicate or zeolite or both).

All the above exemplified pads/pantiliners delivered outstanding odour control benefits for prolonged period of time when in use, typically when coming into contact with for example bodily fluids while delivering effective protection as well as cleanness and dryness benefit. Also these pads/pantiliners were able to minimize the occurrence of skin problems. The pads/pantiliners comprising spores showed outstanding stability upon prolonged period of storage

What is claimed is:

1. A disposable article comprising a liquid pervious topsheet and a backsheet, an absorbent core being intermediate to said backsheet and said tonsheet; said absorbent core comprising at least a spore which has the ability to germinate into a microorganism which exhibits antagonistic properties against undesirable strains of microorganisms.

2. An article according to claim 1 wherein said article is a sanitary napkin, a pantiliner, a tampon, a diaper, an incontinent pad, a breast pad, a human or animal waste management device, a perspiration pad or an interlabial pad.

3. An article according to claim 1 wherein the spore-forming micro-organism exhibiting antagonistic properties against undesirable strains of micro-organisms is a species of the genius *Bacillus* and/or of the genius *Sporolactobacillus* and mixtures thereof and/or wherein the spore is of said spore-forming micro-organism.

4. An article according to claim 1, which further comprises an absorbent gelling material.

5. An article according to claim 4 which comprise the absorbent gelling material at a level of from 30 $gm^{-2}$ to 110 $gm^{-2}$.

6. An article according to claim 1, which further comprises an additional odour control agent.

7. An article according to claim 6, wherein the level of the additional odour control agent or mixture thereof is from 0 $gm^{-2}$ to 600 $gm^{-2}$.

* * * * *

UNITED STATES PATENT AND TRADEMARK OFFICE
CERTIFICATE OF CORRECTION

PATENT NO. : 6,967,025 B2  Page 1 of 1
DATED : November 22, 2005
INVENTOR(S) : Achille Di Cintio et al.

It is certified that error appears in the above-identified patent and that said Letters Patent is hereby corrected as shown below:

Column 6,
Line 23, "lifters" should read -- litters --.

Column 12,
Line 65, "Goffingen" should read -- Gottingen --.

Column 17,
Line 34, "!"activated"" should read -- "activated" --.

Column 26,
Line 8, "tonsheet" should read -- topsheet --.

Signed and Sealed this

Fourth Day of April, 2006

JON W. DUDAS
*Director of the United States Patent and Trademark Office*